US012709763B2

(12) United States Patent
Tsukamoto et al.

(10) Patent No.: US 12,709,763 B2
(45) Date of Patent: Aug. 18, 2026

(54) METHOD OF PRODUCING CARBOXYLIC ACID

(71) Applicant: Toray Industries, Inc., Tokyo (JP)

(72) Inventors: Daijiro Tsukamoto, Kamakura (JP); Kenji Kawamura, Kamakura (JP); Katsushige Yamada, Kamakura (JP)

(73) Assignee: Toray Industries, Inc., Tokyo (JP)

(*) Notice: Subject to any disclaimer, the term of this patent is extended or adjusted under 35 U.S.C. 154(b) by 640 days.

(21) Appl. No.: 17/439,838

(22) PCT Filed: Mar. 24, 2020

(86) PCT No.: PCT/JP2020/012856

§ 371 (c)(1),
(2) Date: Sep. 16, 2021

(87) PCT Pub. No.: WO2020/196460

PCT Pub. Date: Oct. 1, 2020

(65) Prior Publication Data

US 2022/0090148 A1 Mar. 24, 2022

(30) Foreign Application Priority Data

Mar. 25, 2019 (JP) ................................ 2019-056709

(51) Int. Cl.
*C12P 7/40* (2006.01)
*B01D 11/04* (2006.01)
*B01D 61/02* (2006.01)
*C12R 1/19* (2006.01)

(52) U.S. Cl.
CPC ............ *C12P 7/40* (2013.01); *B01D 11/0415* (2013.01); *B01D 61/027* (2013.01); *C12R 2001/19* (2021.05)

(58) Field of Classification Search
CPC .. B01D 11/0415; B01D 11/04; B01D 61/027; B01D 61/02; C12P 7/40; C12P 7/42;
(Continued)

(56) References Cited

U.S. PATENT DOCUMENTS

2011/0263811 A1* 10/2011 Sawai .................. B01D 61/027 435/139
2017/0362156 A1* 12/2017 Binder ..................... B01D 3/02

FOREIGN PATENT DOCUMENTS

CN 106117292 A 11/2016
CN 106905142 A 6/2017
(Continued)

OTHER PUBLICATIONS

JP 2010126512 A English description, JP 2010126512 A, Kawamura Kenji et al.*

(Continued)

*Primary Examiner* — Akash K Varma
(74) *Attorney, Agent, or Firm* — DLA Piper LLP (US)

(57) ABSTRACT

Efficient production of a carboxylic acid is provided by a method of producing a carboxylic acid, which includes the following steps (A) and (B): (A) filtering a carboxylic acid-containing fermentation broth by passing said fermentation broth through a nanofiltration membrane, to obtain a carboxylic acid-containing filtrate from the permeate side of the membrane; and (B) extracting the carboxylic acid from the carboxylic acid-containing filtrate obtained in the step (A) using an extraction solvent which undergoes phase separation with the filtrate, and collecting a carboxylic acid extract phase-separated from the aqueous phase.

4 Claims, 2 Drawing Sheets

Immediately after shaking

(58) Field of Classification Search
CPC ...... C12P 7/44; C12P 7/46; C12P 7/54; C12P 7/00; C12P 7/56; C12P 13/222; C12P 13/22; C12R 2001/19; C12R 1/19; C12N 1/02; C07B 63/00; C07C 51/47; C07C 51/48; C07C 227/40; C07C 53/08; C07C 55/10; C07C 55/14; C07C 55/08; C07C 57/13; C07C 57/16; C07C 65/03; C07C 229/36; C07C 201/00
USPC ........................................................ 210/653
See application file for complete search history.

(56) References Cited

FOREIGN PATENT DOCUMENTS

| | | | | | |
|---|---|---|---|---|---|
| EP | 0247436 A1 | * | 5/1987 | | C07C 99/02 |
| JP | S62-201606 A | | 9/1987 | | |
| JP | S62-277349 A | | 12/1987 | | |
| JP | H09-500649 A | | 1/1997 | | |
| JP | 2010-095450 A | | 4/2010 | | |
| JP | 2010126512 A | * | 6/2010 | | C07C 51/43 |
| JP | 2015-119738 A | | 7/2015 | | |
| JP | 2017-537908 A | | 12/2017 | | |
| WO | 95/03268 | | 2/1995 | | |
| WO | 2010/074222 A1 | | 7/2010 | | |

OTHER PUBLICATIONS

Extended European Search Report dated Dec. 5, 2022, of counterpart European Patent Application No. 20778573.4.
Notice of Reasons for Refusal dated Apr. 16, 2024, of counterpart Japanese Patent Application No. 2020-546518, along with an English machine translation.

* cited by examiner

Immediately after shaking

Immediately after shaking 12 hours after shaking

METHOD OF PRODUCING CARBOXYLIC ACID

TECHNICAL FIELD

This disclosure relates to a method of producing a carboxylic acid from a carboxylic acid-containing fermentation broth.

BACKGROUND

Conventionally, extraction separation is often used as a means for recovering carboxylic acids from fermentation broths containing carboxylic acids, along with adsorption separation with anion exchange resins, electrodialysis, crystallization and the like. In the extraction of a carboxylic acid from a fermentation broth containing the carboxylic acid, a phenomenon is known in which an intermediate phase containing solids that do not dissolve either in the fermentation broth (aqueous phase) or an extraction solvent (organic phase) is produced at the phase interface between the aqueous phase and the organic phase. Since this phenomenon interferes with the phase separation during the extraction, it is known to cause ill effects such as the necessity to additionally perform a solid removal step. Methods using membrane filtration have already been proposed as means for solving such problems. For example, JP S62-277349 A discloses that, when recovering an amino acid from an amino acid fermentation broth by extraction, it is possible to remove cytoplasm and other solids and speed up the phase separation of the amino acid fermentation broth and an extraction solvent by passing the amino acid fermentation broth through an ultrafiltration membrane (UF membrane) through which molecules having a molecular weight of 1,000 or less permeate, in the pre-stage of the extraction of the amino acid. Further, JP 2015-119738 A discloses that, when recovering an aliphatic dicarboxylic acid from an aliphatic dicarboxylic acid fermentation broth by extraction, it is possible to remove microorganisms and speed up the phase separation of the aliphatic dicarboxylic acid fermentation broth and an extraction solvent by passing the aliphatic dicarboxylic acid fermentation broth through a microfiltration membrane (MF membrane), and that a microfiltration membrane is more suitable than an ultrafiltration membrane as a filtration membrane. In addition, JP 2010095450 A discloses that passing a monocarboxylic acid fermentation broth through a nanofiltration membrane enables to remove impurities and to increase the purity of the monocarboxylic acid to be recovered.

JP '349 and JP '738 disclose that the phase separation during the extraction is sped up by passing the fermentation liquids through an ultrafiltration membrane and a microfiltration membrane, respectively. However, we found out that the phase separation between the aqueous phase and the organic phase during the extraction cannot be sufficiently achieved even when a carboxylic acid-containing fermentation broth is passed through both a microfiltration membrane and an ultrafiltration membrane (corresponds to Comparative Example 1 herein).

Therefore, it could be helpful to provide a method of enhancing the phase separability between the aqueous phase and the organic phase during the extraction of a carboxylic acid from a carboxylic acid-containing fermentation broth.

SUMMARY

Although the method of passing a monocarboxylic acid-containing fermentation broth through a nanofiltration membrane to increase the purity of the monocarboxylic acid to be recovered is known as described above, prior methods do not suggest the effects of the nanofiltration membrane treatment on the extraction process of the carboxylic acid, and rather suggest that the nanofiltration membrane whose pore size is smaller than that of an ultrafiltration membrane is less suitable than the ultrafiltration membrane. However, we found out that the phase separation between the aqueous phase and the organic phase after the extraction is accelerated by passing a carboxylic acid fermentation broth through a nanofiltration membrane before subjecting the fermentation broth to the extraction process of a carboxylic acid.

We thus provide (1) to (5):

(1) A method of producing a carboxylic acid, including the following steps (A) and (B):

(A) filtering a carboxylic acid-containing fermentation broth by passing the fermentation broth through a nanofiltration membrane, to obtain a carboxylic acid-containing filtrate from the permeate side of the membrane; and (B) extracting the carboxylic acid from the carboxylic acid-containing filtrate obtained in the step (A) using an extraction solvent which undergoes phase separation with the filtrate, and collecting a carboxylic acid extract phase-separated from the aqueous phase.

(2) The method of producing a carboxylic acid according to (1), wherein the pH of the carboxylic acid-containing fermentation broth and/or the carboxylic acid-containing filtrate is adjusted to 4.5 or less.

(3) The method of producing a carboxylic acid according to (1) or (2), including the step of removing insoluble substances before passing the carboxylic acid-containing fermentation broth through the nanofiltration membrane in the step (A).

(4) The method of producing a carboxylic acid according to (3), wherein the step of removing the insoluble substances is the step of passing the carboxylic acid-containing fermentation broth through a microfiltration membrane.

(5) The method of producing a carboxylic acid according to any one of (1) to (4), wherein the carboxylic acid has a molecular weight of 200 or less.

It is thus possible, when recovering a carboxylic acid from a carboxylic acid-containing fermentation broth by extraction, to accelerate the phase separation between the aqueous phase and the organic phase after the extraction, and efficiently produce the carboxylic acid.

DETAILED DESCRIPTION

Figure 1:
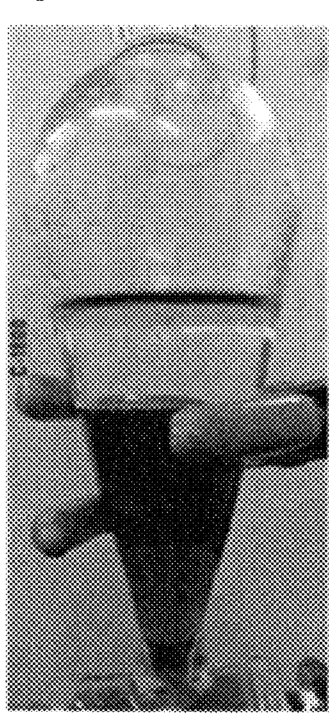
FIG. 1 shows a photograph immediately after bringing a carboxylic acid-containing filtrate obtained by being passed through a nanofiltration membrane into contact with an extraction solvent, in the extraction test of carboxylic acids from the carboxylic acid-containing filtrate.

Our methods will now be described in more specific detail. It is noted, however, that this disclosure is in no way limited to the following examples.

The term "carboxylic acid" generally refers to a compound having one or a plurality of carboxyl groups (COOH groups) in the molecule. The carboxylic acid is not particularly limited, but is preferably a carboxylic acid having a molecular weight of about 200 or less since such a carboxylic acid is highly permeable through a nanofiltration membrane to be described later. Specific examples of preferred carboxylic acids include formic acid, acetic acid, propionic acid, oxalic acid, glycolic acid, gluconic acid, acrylic acid, butyric acid, isobutyric acid, γ-aminobutyric acid, valeric acid, isovaleric acid, pyruvic acid, lactic acid, hydroxybutyric acid, succinic acid, fumaric acid, maleic acid, itaconic acid, malic acid, tartaric acid, oxaloacetic acid, glutaric acid, 2-oxoglutaric acid, adipic acid, adipic semialdehyde, 3-oxoadipic acid, 3-hydroxyadipic acid, 3-hydroxyadipic acid-3,6-lactone, α-hydromuconic acid, β-hydromuconic acid, muconic acid, muconolactone, 2-keto-L-gluonic acid, 6-aminocaproic acid, aconitic acid, benzoic acid, 4-hydroxybenzoic acid, phenylacetic acid, terephthalic acid, isophthalic acid, shikimic acid, phenylalanine, tyrosine and histidine.

The term "carboxylic acid-containing fermentation broth" includes not only a culture liquid in which a carboxylic acid(s) has/have been produced by the action of microorganisms in a liquid medium containing fermentation raw materials such as a carbon source(s), a nitrogen source(s), an inorganic salt(s), an amino acid(s), a vitamin(s) and/or the like, but also one obtained by adding a carboxylic acid(s) chemically or biologically synthesized separately, to a culture liquid in which microorganisms have been cultured in a liquid medium containing the fermentation raw materials.

Examples of the carbon source to be used to culture microorganisms include: monosaccharides such as glucose, sucrose, fructose, galactose, mannose, xylose and arabinose; disaccharides and polysaccharide, in which any of these monosaccharides are bound; and molasses, sugar beet syrup, cane molasses, black treacle, starch saccharified solution and cellulose-containing biomass saccharified solution, which contain any of the above saccharides. Examples of the nitrogen source to be used include ammonia gas, ammonia water, ammonium salts, urea, nitric acid salts, other organic nitrogen sources supplementarily used such as oil cakes, soybean hydrolyzates, casein degradation products, other amino acids, vitamins, corn steep liquor, yeast and yeast extracts, meat extracts, and peptides such as peptone. Examples of the inorganic salt to be used include phosphoric acid salts, magnesium salts, calcium salts, iron salts and manganese salts, any of which can be added as appropriate. In addition, it is also possible to use a waste biomass as a fermentation raw material which contains any of these carbon sources, nitrogen sources, inorganic salts, amino acids, vitamins and the like. Examples of the waste biomass include food wastes, livestock manure, sewage sludge, agricultural residues and wood wastes.

Examples of the microorganisms to be used in the preparation of the carboxylic acid-containing fermentation broth include: yeasts such as baker's yeast; bacteria such as *Escherichia coli* and coryneform bacteria; filamentous fungi; and actinomycetes, but not particularly limited thereto. The microorganisms to be used may be those isolated from natural environments, or those whose properties are partially modified by mutation or genetic engineering.

Step (A)

First, as the step (A), a carboxylic acid-containing fermentation broth is passed through a nanofiltration membrane to obtain a carboxylic acid-containing filtrate.

The expression "to pass (a carboxylic acid-containing fermentation broth) through a nanofiltration membrane" refers to passing a carboxylic acid-containing fermentation broth through a nanofiltration membrane to collect a permeate containing a carboxylic acid from the permeate side of the membrane. Further, the permeate that has been passed through the nanofiltration membrane and contains the carboxylic acid is referred to as "carboxylic acid-containing filtrate."

By passing the carboxylic acid-containing fermentation broth through the nanofiltration membrane, formation of an intermediate phase containing solids that do not dissolve either in the aqueous phase or the organic phase is inhibited, after extracting the carboxylic acid in the subsequent step (B), and the phase separation between the aqueous phase and the organic phase is accelerated.

The carboxylic acid in the carboxylic acid-containing fermentation broth may be dissolved in water as the carboxylic acid or a salt of the carboxylic acid. Examples of the salt of the carboxylic acid include lithium salts, sodium salts, potassium salts, magnesium salts, calcium salts and ammonium salts. The salt of the carboxylic acid may be a mixture of different kinds of such salts.

The concentration of the carboxylic acid in the carboxylic acid-containing fermentation broth to be filtered by being passed through the nanofiltration membrane is not particularly limited. However, a higher carboxylic acid concentration in the fermentation broth leads to a higher carboxylic acid concentration in the resulting carboxylic acid-containing filtrate, and thus is suitable to reduce the energy required in performing concentration. To increase the concentration of the carboxylic acid, that is, to perform concentration, it is possible to use evaporative concentration in which moisture is removed by evaporation, reverse osmosis membrane concentration in which moisture is removed by being passed through a reverse osmosis membrane, or a combination of these methods.

As the material of the nanofiltration membrane, it is possible to use a polymeric material such as a cellulose acetate-based polymer, a polyamide, a polyester, a polyimide or a vinyl polymer. The nanofiltration membrane is not limited to a membrane made of one kind of the materials described above, and may be a membrane containing a plurality of membrane materials. Further, the nanofiltration membrane may be either of the followings: an asymmetrical membrane having a membrane structure that includes a dense layer on at least one surface of the membrane, and in which the diameter of pores in the membrane gradually increase in the direction from the dense layer toward the interior of the membrane or toward the other surface of the membrane; or a composite membrane having a membrane structure which includes an extremely thin functional layer made of another material, on the dense layer of the asymmetrical membrane. As the composite membrane, a composite membrane disclosed in JP 62-201606 A, and in which a nanofiltration membrane composed of a polyamide functional layer is formed on a support membrane whose membrane material is polysulfone, can be used.

Among these, a composite membrane including a polyamide functional layer having a high pressure resistance, a high water permeability and a high solute-removal ability, in combination, and having a high potential, is preferred. Further, to maintain durability against the operating pressure, a high water permeability and blocking performance, a composite membrane having a structure which includes a polyamide functional layer and in which the polyamide functional layer is supported by a support composed of a porous membrane or a nonwoven fabric, is preferred. In the nanofiltration membrane including a polyamide functional layer, examples of preferred carboxylic acid components of the monomers constituting the polyamide include aromatic carboxylic acids such as trimesic acid, benzophenonetetracarboxylic acid, trimellitic acid, pyromellitic acid, isophthalic acid, terephthalic acid, naphthalenedicarboxylic acid, diphenylcarboxylic acid and pyridinecarboxylic acid. Among these, trimesic acid, isophthalic acid, terephthalic acid, or a mixture thereof is more preferred, taking into consideration the solubility in a membrane-forming solvent.

Examples of preferred amine components of the monomers constituting the polyamide include: primary diamines containing an aromatic ring such as m-phenylenediamine, p-phenylenediamine, benzidine, methylenebisdianiline, 4,4'-diaminobiphenyl ether, dianisidine, 3,3',4-triaminobiphenyl ether, 3,3',4,4'-tetraaminobiphenyl ether, 3,3'-dioxybenzidine, 1,8-naphthalenediamine, m(p)-monomethylphenylenediamine, 3,3'-monomethylamino-4,4'-diaminobiphenyl ether, 4,N,N'-(4-amino benzoyl)-p(m)-phenylenediamine-2,2'-bis(4-aminophenylbenzimidazole), 2,2'-bis(4-aminophenylbenzoxazole) and 2,2'-bis(4-aminophenylbenzothiazole); and secondary diamines such piperazine, piperidine, and derivatives thereof. In particular, a nanofiltration membrane that includes a functional layer made of a crosslinked polyamide containing piperazine or piperidine as a monomer, is preferably used because such a membrane has heat resistance and chemical resistance in addition to the pressure resistance and durability. More preferred is a nanofiltration membrane containing the above-described crosslinked piperazine polyamide or a crosslinked piperidine polyamide as a main component. Examples of the nanofiltration membrane which includes a functional layer made of a polyamide containing piperazine polyamide include those disclosed in JP 62-201606 A. Specific examples thereof include crosslinked piperazine polyamide-based semipermeable membranes, UTC-60 and UTC-63, manufactured by Toray Industries, Inc.

As a spiral nanofiltration membrane element, it is also possible to use a nanofiltration membrane module, SU-210, SU-220, SU-600 or SU-610, manufactured by Toray Industries, Inc., that includes UTC-60 or UTC-63 including a functional layer made of a crosslinked piperazine polyamide, manufactured by Toray Industries, Inc. Examples of the nanofiltration membrane also include: NF-45, NF-90, NF-200 and NF-400, which are nanofiltration membranes including a functional layer made of a crosslinked piperazine polyamide and manufactured by FilmTec Corporation; NF99, NF97 and NF99HF, which are nanofiltration membranes including a polyamide functional layer and manufactured by Alfa Laval Inc.; and GEsepa, which is a cellulose acetate-based nanofiltration membrane, manufactured by GE Osmonics Inc.

Filtration of the carboxylic acid-containing fermentation broth by the nanofiltration membrane may be carried out while applying pressure. The filtration pressure to be used in the filtration is not particularly limited. However, a filtration pressure of 0.1 MPa or more and 8 MPa or less is preferably used, because a filtration pressure lower than 0.1 MPa results in a decreased membrane permeation rate, and a filtration pressure higher than 8 MPa has an impact on the damage of the membrane. Further, a filtration pressure of 0.5 MPa or more and 7 MPa or less leads to a high membrane permeation flux, and allows for an efficient permeation of the carboxylic acid, and thus is more preferred.

In the filtration of the carboxylic acid-containing fermentation broth with the nanofiltration membrane, the recovery rate of the carboxylic acid can be improved by allowing the non-permeate to return to raw water again, and to perform filtration repeatedly.

Since the nanofiltration membrane has a characteristic that a substance which is non-ionized (undissociated) in a solution more easily permeates therethrough compared to a substance which is ionized (dissociated) in the solution, adjusting the pH of the carboxylic acid-containing fermentation broth to an acidic pH leads to an increase in the amount of carboxylic acid which is in the form of the carboxylic acid, not in the form of a carboxylic acid salt, thereby facilitating the permeation of the carboxylic acid through the nanofiltration membrane. On the other hand, too low a pH leads to the risk of corrosion of the apparatus used, making it industrially disadvantageous. From these points of view, the pH of the carboxylic acid-containing fermentation broth to be passed through the nanofiltration membrane is preferably adjusted to a pH of 4.5 or less, more preferably a pH of 1.5 or more and 4.5 or less, and still more preferably a pH of 2.0 or more and 4.0 or less.

An acid to adjust the pH of the carboxylic acid-containing fermentation broth to be passed through the nanofiltration membrane is not particularly limited as long as the fermentation broth can be adjusted to an acidic pH, and a mineral acid such as sulfuric acid, hydrochloric acid, nitric acid, phosphoric acid or boric acid can be preferably used.

The carboxylic acid-containing fermentation broth contains insoluble substances derived from bacterial cells, unutilized fermentation raw materials and the like, and biological substances such as proteins, secreted from microorganisms. From the viewpoint of reducing the clogging of the nanofiltration membrane, it is preferred to remove the insoluble substances in the carboxylic acid-containing fermentation broth, before performing the nanofiltration membrane treatment described above. Further, it is more preferred to remove the biological substances such as proteins, in the carboxylic acid-containing fermentation broth, along with the removal of the insoluble substances.

The insoluble substances in the carboxylic acid-containing fermentation broth can be removed, for example, by a method of passing the carboxylic acid-containing fermentation broth through a microfiltration membrane (MF membrane), and as a result, the carboxylic acid-containing fermentation broth from which the insoluble substances have been removed can be obtained from the permeate side of the membrane. Alternatively, the carboxylic acid-containing fermentation broth can be subjected to centrifugation to allow the insoluble substances to settle, and the resulting supernatant can be collected to obtain the carboxylic acid-containing fermentation broth from which the insoluble substances have been removed. The step of removing the insoluble substances by a microfiltration membrane is preferably used.

The microfiltration membrane is not particularly limited as long as the membrane has a function to remove insoluble substances derived from bacterial cells, unutilized fermentation raw materials and the like. As the material of the microfiltration membrane, it is possible to use, for example, a porous ceramic membrane, a porous glass membrane, a porous organic polymer membrane, a metal fiber-knitted or woven body, a nonwoven fabric or the like. Among these, a porous organic polymer membrane or a porous ceramic membrane is particularly suitable.

The microfiltration membrane preferably has, for example, a configuration including a porous resin layer as a functional layer, from the viewpoint of fouling resistance.

The microfiltration membrane including a porous resin layer preferably has a porous resin layer which functions as a functional layer, on the surface of a porous substrate.

The material of the porous substrate is composed of an organic material and/or an inorganic material or the like, and an organic fiber is desirably used. The porous substrate to be used is preferably a woven fabric or a nonwoven fabric obtained using an organic fiber such as a cellulose fiber, a cellulose triacetate fiber, a polyester fiber, a polypropylene fiber or a polyethylene fiber, and more preferably a nonwoven fabric whose density can be controlled relatively easily, and which can also be produced easily and is inexpensive.

An organic polymer membrane can be suitably used as the porous resin layer. Examples of the material of the organic polymer membrane include polyethylene-based resins, polypropylene-based resins, polyvinyl chloride-based resins, polyvinylidene fluoride-based resins, polysulfone-based resins, polyethersulfone-based resins, polyacrylonitrile-based resins, cellulose-based resins and cellulose triacetate-based resins. The organic polymer membrane may be made of a mixture of resins containing any of these resins as a main component. The term "main component" as used herein refers to a component contained in an amount of 50% by weight or more, preferably 60% by weight or more. The material of the organic polymer membrane to be used is preferably a polyvinyl chloride-based resin, a polyvinylidene fluoride-based resin, a polysulfone-based resin, a polyethersulfone-based resin or a polyacrylonitrile-based resin, which can be easily formed into a membrane using a solution and which has an excellent physical durability and chemical resistance, and most preferably a polyvinylidene fluoride-based resin or a resin containing the same as a main component.

A homopolymer of vinylidene fluoride is preferably used as the polyvinylidene fluoride-based resin. Further, a copolymer of vinylidene fluoride and a vinyl monomer copolymerizable with vinylidene fluoride is also preferably used as the polyvinylidene fluoride-based resin. Examples of the vinyl monomer copolymerizable with vinylidene fluoride include tetrafluoroethylene, hexafluoropropylene and ethylene trichloride fluoride.

The biological substances such as proteins in the carboxylic acid-containing fermentation broth can be removed, for example, by a method of passing the carboxylic acid-containing fermentation broth through an ultrafiltration membrane (UF membrane), and as a result, the carboxylic acid-containing fermentation broth from which the biological substances such as proteins have been removed can be obtained from the permeate side of the membrane.

The ultrafiltration membrane preferably has a molecular weight cutoff of 5,000 to 100,000, and more preferably 5,000 to 30,000, but not particularly limited thereto, as long as the molecular weight cutoff is 2,000 to 100,000.

It is possible to use as the material of the ultrafiltration membrane, polyethersulfone, polysulfone, polyacrylonitrile, polyvinylidene fluoride, regenerated cellulose, cellulose, a cellulose ester, a sulfonated polysulfone, a sulfonated polyethersulfone, a polyolefin, polyvinyl alcohol, polymethyl methacrylate, poly(ethylene tetrafluoride) or the like.

Specific examples of the ultrafiltration membrane to be used include: M series, P series, as well as GH (G-10) type, GK (G-20) type and GM (G-50) type of G series, and HWS UF type and STD UF type of "DURATHERM" (registered trademark) series, of DESAL brand, manufactured by GE W&PT; VT, MT, ST, SM, MK, MW, LY, BN and BY, manufactured by Synder Filtration Inc; UF series of "Microza" (registered trademark), manufactured by Asahi Kasei Corporation; and NTR-7410 and NTR-7450, manufactured by Nitto Denko Corporation.

The order of removing insoluble substances derived from bacterial cells, fermentation raw materials and the like, and biological substances such as proteins, is not particularly limited. However, it is preferred to first remove the insoluble substances derived from bacterial cells, fermentation raw materials and the like, that have a large size, because it allows for reducing the clogging of the ultrafiltration membrane.

Step (B)

As the step (B), the carboxylic acid is extracted from the carboxylic acid-containing filtrate obtained in the step (A) using an extraction solvent that undergoes phase separation with the filtrate, and a carboxylic acid extract phase-separated from the aqueous phase is collected.

The extraction solvent to be used in the step (B) is not particularly limited as long as the solvent undergoes phase separation with the carboxylic acid-containing filtrate obtained in the step (A) and allows for extracting the carboxylic acid. Examples of the extraction solvent include: aliphatic hydrocarbon-based extraction solvents such as pentane, hexane and heptane; aromatic hydrocarbon-based extraction solvents such as benzene, toluene and xylene; chlorine-based extraction solvents such as tetrachloride, chloroform, dichloromethane and trichloroethylene; ester-based extraction solvents such as ethyl acetate and butyl acetate; ketone-based extraction solvents such as methyl ethyl ketone, methyl isobutyl ketone, cyclopentanone and cyclohexanone; ether-based extraction solvents such as dimethyl ether, diethyl ether, diisopropyl ether and dibutyl ether; extraction solvents based on alcohols having 4 or more carbon atoms such as butanol, hexanol, octanol, decanol and oleyl alcohol; isopropanol mixture-based extraction solvents such as chloroform/isopropanol mixed solutions, dichloromethane/isopropanol mixed solutions and ethyl acetate/isopropanol mixed solutions; long-chain amine-based extraction solvents such as trioctylamine, trinonylamine and tridecylamine; alkyl phosphine oxide-based extraction solvents such as tributylphosphine oxide and trioctylphosphine oxide; and ionic liquid-based extraction solvents such as ammonium-based, imidazolium-based, phosphonium-based, pyridinium-based, pyrrolidinium-based and sulfonium-based extraction solvents. These extraction solvents may be used singly, or as a mixture of two or more kinds thereof.

When using a chloroform/isopropanol mixed solution, a dichloromethane/isopropanol mixed solution or an ethyl acetate/isopropanol mixed solution as the extraction solvent, the percentage of isopropanol to be mixed is preferably 40% by volume or less. When the percentage of isopropanol to be mixed is too high, the phase separability of the extraction solvent from the carboxylic acid-containing filtrate tends to decrease.

The extraction temperature in the step (B) is not particularly limited. However, from the viewpoint that the extraction temperature is preferably within the temperature range in which the carboxylic acid-containing filtrate and the extraction solvent do not solidify or boil, the extraction temperature is more preferably 5° C. or higher and 100° C. or lower, still more preferably 10° C. or higher and 90° C. or lower, and particularly preferably 20° C. or higher and 80° C. or lower.

In the step (B), the pH of the carboxylic acid-containing filtrate is not particularly limited, as long as the pH is less than 7, which is an acidic condition. However, a lower pH is more preferred, because there is a tendency that a carboxylic acid which is not in the form of a carboxylic acid salt is more easily extracted into the extraction solvent. On the other hand, too low a pH leads to the risk of corrosion of the apparatus used, making it industrially disadvantageous. From these points of view, the pH of the carboxylic acid-containing filtrate in the step (B) is preferably adjusted to a pH of 4.5 or less, more preferably a pH of 1.5 or more and 4.5 or less, and still more preferably a pH of 2.0 or more and 4.0 or less.

An acid to be used to adjust the pH of the carboxylic acid-containing filtrate in the step (B) is not particularly limited as long as the filtrate can be adjusted to an acidic pH, and a mineral acid such as sulfuric acid, hydrochloric acid, nitric acid, phosphoric acid or boric acid, which is preferably used for adjusting the pH in the step (A), can be preferably used.

The carboxylic acid concentration in the carboxylic acid-containing filtrate to be subjected to the step (B) is not particularly limited. However, a higher carboxylic acid concentration tends to facilitate the migration of the carboxylic acid into the extraction solvent. Specifically, the carboxylic acid concentration is preferably 0.01% by weight or more, more preferably 0.1% by weight or more, still more preferably 1% by weight or more, and particularly preferably 20% by weight or more. To increase the concentration of the carboxylic acid, that is, to perform concentration, it is possible to use evaporative concentration in which moisture is removed by evaporation, reverse osmosis membrane concentration in which moisture is removed by being passed through a reverse osmosis membrane, or a combination of these methods. Alternatively, the concentration of the carboxylic acid-containing filtrate may be adjusted to a desired concentration, by adjusting the concentration the carboxylic acid-containing fermentation broth to be subjected to the step (A) as appropriate.

By bringing the resulting raffinate, which is the remaining aqueous phase after the carboxylic acid has been extracted by the extraction solvent, into contact with a fresh extraction solvent, the carboxylic acid remaining in the raffinate can further be recovered, enabling to increase the recovery rate of the carboxylic acid. The raffinate in which the carboxylic acid concentration is sufficiently decreased may be used as water, for the adjustment of the carboxylic acid-containing fermentation broth, or may be purged outside the system.

The extraction can be carried out by batch extraction, simple multiple extraction, countercurrent multi-stage extraction or the like. To continuously carry out extraction at an industrial scale, it is possible to use a mixer-settler extractor, or a column extractor such as a perforated-plate extraction column, a pulsed column or a mixer-settler column.

Subsequent Step

Recovery of the carboxylic acid from the carboxylic acid extract can be carried out by a conventional method such as, for example, a method of simply removing the extraction solvent by evaporation, a method of recovering the carboxylic acid by distillation, a method of precipitating the carboxylic acid, followed by solid-liquid separation, or a method in which the carboxylic acid is back-extracted into water, and then separated from water by distillation, concentration or precipitation.

The extraction solvent removed from the extract may be reused as it is, as the extraction solvent in the step (B), or may be purified by distillation and then reused as the extraction solvent in the step (B). When the extraction solvent is purified by distillation, it is possible to increase the amount of the carboxylic acid recovered by recovering a trace amount of carboxylic acid contained in the extraction solvent.

Other Steps

The carboxylic acid can be concentrated by passing the carboxylic acid-containing fermentation broth to be subjected to the step (A), the carboxylic acid-containing filtrate to be subjected to the step (B), an aqueous solution containing the carboxylic acid which may be produced in the post-step of the step (B) or the like, through a reverse osmosis membrane (RO membrane). The expression "to pass (a liquid) through a reverse osmosis membrane" refers to filtering any of the liquids as described above by passing the liquid through a reverse osmosis membrane, to remove water from the permeate side of the membrane, and to collect an aqueous solution containing the carboxylic acid in which the carboxylic acid concentration is increased, from the non-permeate side.

As the membrane material of the reverse osmosis membrane, it is possible to use a polymeric material such as a cellulose acetate-based polymer, a polyamide, a polyester, a polyimide or a vinyl polymer, which is generally available on the market. The reverse osmosis membrane is not limited to a membrane made of one kind of the above-mentioned materials, and may be a membrane containing a plurality of such membrane materials. The reverse osmosis membrane to be used can be in any appropriate form such as a flat membrane, a spiral membrane or a hollow fiber membrane.

Specific examples of the reverse osmosis membrane include: (UTC) SU-710, SU-720, SU-720F, SU-710L, SU-720L, SU-720LF, SU-720R, SU-710P, SU-720P, SU-810, SU-820, SU-820L and SU-820FA, which are polyamide-based reverse osmosis membranes, manufactured by Toray Industries, Inc.; SC-L100R, SC-L200R, SC-1100, SC-1200, SC-2100, SC-2200, SC-3100, SC-3200, SC-8100 and SC-8200, which are cellulose acetate-based reverse osmosis membranes, manufactured by Toray Industries, Inc.; NTR-759HR, NTR-729HF, NTR-70SWC, ES10-D, ES20-D, ES20-U, ES15-D, ES15-U and LF10-D, manufactured by Nitto Denko Corporation; RO98pHt, RO99, HR98PP and CE4040C-30D, manufactured by Alfa Laval Inc.; GE Sepa manufactured by GE; and BW30-4040, TW30-4040, XLE-4040, LP-4040, LE-4040, SW30-4040 and SW30HRLE-4040, manufactured by FilmTec Corporation.

Filtration by the reverse osmosis membrane is carried out while applying pressure, and the filtration pressure to be applied is preferably 1 MPa or more and 8 MPa or less, because a filtration pressure lower than 1 MPa causes a decrease in the membrane permeation rate, and a filtration pressure higher than 8 MPa has an impact on the damage of the membrane. The filtration pressure is more preferably 1 MPa or more and 7 MPa or less, and still more preferably 2 MPa or more and 6 MPa or less.

EXAMPLES

Our methods will now be described in more specific detail, with reference to Reference Examples, Examples and Comparative Examples. However, this disclosure is in no way limited to the results of the following examples.

HPLC Analysis Conditions

HPLC analysis was performed under the following analysis conditions:

Column 1: Synergi Polar-RP (manufactured by Phenomenex Inc.)

Column 2: Synergi Hydro-RP (manufactured by Phenomenex Inc.)

Column temperature: 45° C.

Mobile phase 1: 5 mM formic acid aqueous solution/acetonitrile=98/2 (vol/vol), 1 mL/min Mobile phase 2: an aqueous solution of (5 mM formic acid, 20 mM Bis-Tris and 0.1 mM EDTA-2Na)/acetonitrile=98/2 (vol/vol), 1 mL/min Detection: electrical conductivity.

Method of Analyzing pH

A Horiba pH meter F-52 (manufactured by HORIBA, Ltd.) was used. The pH calibration was carried out using a pH 4.01 standard solution (manufactured by FUJIFILM Wako Pure Chemical Corporation), a pH 6.86 standard solution (manufactured by FUJIFILM Wako Pure Chemical Corporation), and a pH 9.18 standard solution (manufactured by FUJIFILM Wako Pure Chemical Corporation).

Reference Example 1: Preparation of Carboxylic Acid-Containing Fermentation broth (Acetic Acid and Succinic Acid)

A carboxylic acid-containing fermentation broth (model fermentation broth) was prepared by the following procedure. *Escherichia coli* NBRC strain 3301 was inoculated in 5 mL of LB culture medium in a test tube, and cultured with shaking overnight (preculture). The preculture liquid was inoculated in 1 L of a culture medium having the composition shown below, and cultured with shaking in a Sakaguchi flask (capacity: 2 L) for 24 hours. To the resulting culture liquid, acetic acid (manufactured by FUJIFILM Wako Pure Chemical Corporation) and succinic acid (manufactured by FUJIFILM Wako Pure Chemical Corporation) were added such that acetic acid and succinic acid each achieves a concentration of 10 g/L, to obtain a carboxylic acid-containing fermentation broth.

Culture Medium Composition

Glucose: 10 g/L

Ammonium sulfate: 0.5 g/L

Potassium phosphate: 50 mM

Magnesium sulfate: 0.013 g/L

Iron sulphate: 0.032 mg/L

Manganese sulfate: 1.35 mg/L

Calcium chloride: 0.17 mg/L

Sodium chloride: 1.25 g/L

Bacto tryptone: 2.50 g/L

Yeast extract: 1.25 g/L pH: 6.5

Reference Examples 2 to 5

The carboxylic acid-containing fermentation broth prepared in Reference Example 1 was passed through a microfiltration membrane (a porous membrane having a pore size of 0.01 μm or more and less than 1 μm, manufactured by Toray Industries, Inc.), and then passed through an ultrafiltration membrane (molecular weight cutoff: 10,000; manufactured by Toray Industries, Inc.). For each Reference Example, 1 L of the resulting carboxylic acid-containing fermentation broth was transferred to a raw water tank, and passed once through a nanofiltration membrane under the following nanofiltration membrane treatment conditions 1. Each resulting carboxylic acid-containing filtrate lost its color, and was a clear aqueous solution. For each filtrate, the concentrations of the carboxylic acids were analyzed by HPLC, and the permeability of each carboxylic acid was calculated by the following equation. The results of the permeability calculations are shown in Table 1.

Permeability (%)=(compound concentration in permeate)/(compound concentration in raw water)×100.

Reference Examples 6 to 9

Experiments were carried out in the same manner as in Reference Examples 2 to 5, except that concentrated sulfuric acid (manufactured by Sigma-Aldrich Co. LLC) was added to the carboxylic acid-containing fermentation broth after being passed through the ultrafiltration membrane, to adjust the pH to 4.0. Each resulting carboxylic acid-containing filtrate lost its color, and was a clear aqueous solution. The results of the permeability calculations are shown in Table 1.

Reference Examples 10 to 13

Experiments were carried out in the same manner as in Reference Examples 6 to 9, except that the pH was adjusted to 2.0. Each resulting carboxylic acid-containing filtrate lost its color, and was a clear aqueous solution. The results of the permeability calculations are shown in Table 1.

Nanofiltration Membrane Treatment Conditions 1

Separation membrane: UTC-63 (manufactured by Toray Industries, Inc.)

Membrane separation apparatus: "SEPA" (registered trademark) CF-II (manufactured by GE W&PT)

Operating temperature: 25° C.

Filtration pressure: 0.21 to 2.03 MPa

The results of Reference Examples 2 to 13 show that it is possible to obtain a carboxylic acid-containing filtrate, which is a permeate containing the carboxylic acids, by passing the carboxylic acid-containing fermentation broth through the nanofiltration membrane. Further, Examples 2 to 13 show that the permeability of the carboxylic acids is improved by adding an acid at the stage before passing the fermentation broth through the nanofiltration membrane.

TABLE 1

Nanofiltration Membrane Permeation Tests of Carboxylic Acid-containing Fermentation broth

| | pH | Filtration pressure (MPa) | Permeability (%) Acetic Acid | Permeability (%) Succinic Acid |
|---|---|---|---|---|
| Reference Example 2 | 6.5 | 0.21 | 100 | 20 |
| Reference Example 3 | 6.5 | 0.53 | 68 | 14 |
| Reference Example 4 | 6.5 | 0.84 | 87 | 10 |
| Reference Example 5 | 6.5 | 1.25 | 58 | 6 |
| Reference Example 6 | 4.0 | 0.21 | 92 | 80 |
| Reference Example 7 | 4.0 | 0.52 | >99 | >99 |
| Reference Example 8 | 4.0 | 0.95 | >99 | 94 |
| Reference Example 9 | 4.0 | 1.99 | 94 | 80 |
| Reference Example 10 | 2.0 | 0.21 | >99 | 99 |
| Reference Example 11 | 2.0 | 0.53 | >99 | 82 |

TABLE 1-continued

| Nanofiltration Membrane Permeation Tests of Carboxylic Acid-containing Fermentation broth | | | | |
|---|---|---|---|---|
| | | Filtration pressure | Permeability (%) | |
| | pH | (MPa) | Acetic Acid | Succinic Acid |
| Reference Example 12 | 2.0 | 1.03 | >99 | 76 |
| Reference Example 13 | 2.0 | 2.03 | 97 | 65 |

Reference Example 14

A quantity of 1 L of the carboxylic acid-containing fermentation broth prepared in Reference Example 1 was passed through a microfiltration membrane (a porous membrane having a pore size of 0.01 μm or more and less than 1 μm, manufactured by Toray Industries, Inc.), and then passed through an ultrafiltration membrane (molecular weight cutoff: 10,000; manufactured by Toray Industries, Inc.). Thereafter, concentrated sulfuric acid (manufactured by Sigma-Aldrich Co. LLC) was added thereto to adjust the pH to 4.0. The resulting carboxylic acid-containing fermentation broth was transferred to a raw water tank, and passed through a nanofiltration membrane under the following nanofiltration membrane treatment conditions 2.

Nanofiltration Membrane Treatment Conditions 2

Separation membrane: UTC-63 (manufactured by Toray Industries, Inc.)

Membrane separation apparatus: "SEPA" (registered trademark) CF-II (manufactured by GE W&PT)

Operation temperature: 25° C.

Filtration pressure: 0.5 MPa

The resulting carboxylic acid-containing filtrate was concentrated to a final volume of 100 mL, using a rotatory evaporator (manufactured by Tokyo Rikakikai Co., Ltd.). The concentrated aqueous solution had a pH of 4.6. A quantity of 0.5 mL of the resulting aqueous solution and 0.5 mL of dichloromethane (manufactured by FUJIFILM Wako Pure Chemical Corporation) were added to a 2 mL Eppendorf tube, and the resulting mixture was shaken at room temperature for 1 hour at 1,500 rpm, using a Cute Mixer CM-1000 (manufactured by Tokyo Rikakikai Co., Ltd.). After shaking, the concentrations of the carboxylic acids in the aqueous phase were measured by HPLC, and the extraction rate of each carboxylic acid was calculated by the following equation. The results are shown in Table 2.

$$\text{Extraction rate (\%)}=(1-(\text{concentration of compound to be extracted, in raffinate})/(\text{concentration of compound to be extracted, before extraction}))\times 100.$$

Reference Example 15

An experiment was carried out in the same manner as in Reference Example 14, except that ethyl acetate (manufactured by FUJIFILM Wako Pure Chemical Corporation) was used instead of dichloromethane. The results are shown in Table 2.

Reference Example 16

An experiment was carried out in the same manner as in Reference Example 14, except that methyl isobutyl ketone (manufactured by FUJIFILM Wako Pure Chemical Corporation) was used instead of dichloromethane. The results are shown in Table 2.

Reference Example 17

An experiment was carried out in the same manner as in Reference Example 14, except that concentrated sulfuric acid (manufactured by Sigma-Aldrich Co. LLC.) was added to the concentrate of the carboxylic acid-containing filtrate, to adjust the pH to 4.0. The results are shown in Table 2.

Reference Example 18

An experiment was carried out in the same manner as in Reference Example 17, except that ethyl acetate (manufactured by FUJIFILM Wako Pure Chemical Corporation) was used instead of dichloromethane. The results are shown in Table 2.

Reference Example 19

An experiment was carried out in the same manner as in Reference Example 17, except that methyl isobutyl ketone (manufactured by FUJIFILM Wako Pure Chemical Corporation) was used instead of dichloromethane. The results are shown in Table 2.

TABLE 2

| Carboxylic Acid Extraction Tests from Carboxylic Acid-containing Filtrates | | | | |
|---|---|---|---|---|
| | | | Extraction rate (%) | |
| | pH | Extraction solvent | Acetic Acid | Succinic Acid |
| Reference Example 14 | 4.6 | Dichloromethane | 4.8 | 1.1 |
| Reference Example 15 | 4.6 | Ethyl acetate | 29.2 | 8.1 |
| Reference Example 16 | 4.6 | Methyl isobutyl ketone | 21.0 | 10.1 |
| Reference Example 17 | 4.0 | Dichloromethane | 8.5 | 2.4 |
| Reference Example 18 | 4.0 | Ethyl acetate | 40.6 | 31.2 |
| Reference Example 19 | 4.0 | Methyl isobutyl ketone | 31.1 | 25.5 |

The results of Reference Examples 14 to 19 show that the carboxylic acids can be extracted into an extraction solvent from each carboxylic acid-containing filtrate. Further, at the time of extraction, a pH of the carboxylic acid-containing filtrate of 4.5 or lower tends to result in a higher extraction rate.

Example 1

A quantity of 1 L of the carboxylic acid-containing fermentation broth prepared in Reference Example 1 was passed through a microfiltration membrane (a porous membrane having a pore size of 0.01 μm or more and less than 1 μm, manufactured by Toray Industries, Inc.), and then passed through an ultrafiltration membrane (molecular weight cutoff: 10,000; manufactured by Toray Industries, Inc.). Thereafter, concentrated sulfuric acid (manufactured by Sigma-Aldrich Co. LLC) was added thereto to adjust the pH to 4.0. The resulting carboxylic acid-containing fermentation broth was transferred to a raw water tank, and passed through the nanofiltration membrane under the nanofiltration membrane treatment conditions 2 described above. The nanofiltration membrane treatment was carried out continuously by returning the non-permeate to the raw water tank, and adding pure water to the raw water tank if the amount of liquid ran short, to obtain a carboxylic acid-containing filtrate in which the entire amount of the carboxylic acids was recovered, from the permeate side of the membrane. The resulting carboxylic acid-containing filtrate was concentrated to a final volume of 100 mL, using a rotatory evaporator (manufactured by Tokyo Rikakikai Co., Ltd.), and concentrated sulfuric acid (manufactured by Sigma-Aldrich Co. LLC) was added thereto to adjust the pH to 4.0. A quantity of 10 mL of the resulting aqueous solution was transferred to a separatory funnel made of glass (capacity: 50 mL), and 10 mL of ethyl acetate (manufactured by FUJIFILM Wako Pure Chemical Corporation) was added thereto, followed by shaking 30 times. The resulting ethyl acetate phase was collected, 10 mL of ethyl acetate was further added to the raffinate, followed by shaking 30 times, and the resulting ethyl acetate phase was collected. The same operation was repeated, and the extraction of carboxylic acids was performed using a total of 100 mL of ethyl acetate, to obtain a carboxylic acid extract (acetic acid extraction rate: 95%, succinic acid extraction rate: 73%). Formation of an intermediate phase containing solids between the aqueous phase and the ethyl acetate phase was barely observed, in the above extraction, and the phase separation occurred extremely quickly within 10 seconds (FIG. 1).

Comparative Example 1

Figure 2A:
FIGS. 2(*a*) and (*b*) show photographs immediately after (a) and 12 hours after (b) bringing a carboxylic acid-containing fermentation broth which has not been passed through a nanofiltration membrane into contact with an extraction solvent, in the extraction test of carboxylic acids from the carboxylic acid-containing fermentation broth.
Figure 2B:
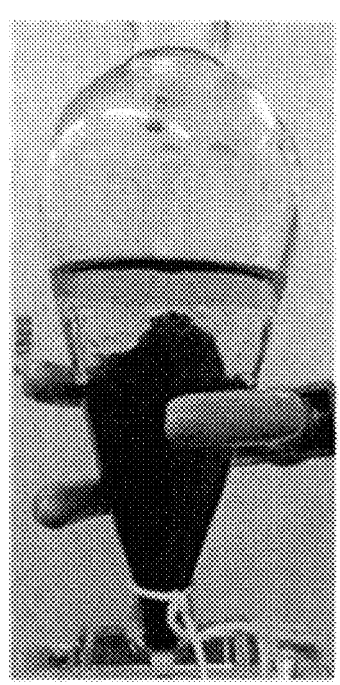

The same procedure as in Example 1 was carried out, except that the carboxylic acid-containing fermentation broth was not passed through a nanofiltration membrane, to obtain a carboxylic acid extract (acetic acid extraction rate: 70%, succinic acid extraction rate: 55%). In this extraction, an intermediate phase containing solids was formed between the aqueous phase and the ethyl acetate phase, and the phase separation did not occur at all immediately after the shaking (FIG. 2). Further, even after being left to stand for 12 hours, the interface between the aqueous phase and the ethyl acetate phase was not clear, although visually observable (FIG. 2). Since it was necessary to collect the ethyl acetate phase such that the intermediate phase was not mixed therein, the amount of the carboxylic acid extract collected decreased compared to that of Example 1.

Example 2

The same procedure as in Example 1 was carried out, except that methyl isobutyl ketone was used as an extraction solvent instead of ethyl acetate, to obtain a carboxylic acid extract (acetic acid extraction rate: 85%, succinic acid extraction rate: 60%). Formation of an intermediate phase containing solids between the aqueous phase and the methyl isobutyl ketone phase was barely observed, in the above extraction, and the phase separation occurred extremely quickly within 10 seconds.

Comparative Example 2

The same procedure as in Example 2 was carried out, except that the carboxylic acid-containing fermentation broth was not passed through a nanofiltration membrane, to obtain a carboxylic acid extract (acetic acid extraction rate: 63%, succinic acid extraction rate: 41%). In this extraction, an intermediate phase containing solids was formed between the aqueous phase and the methyl isobutyl ketone phase, and the phase separation did not occur at all immediately after the shaking. Further, even after being left to stand for 12 hours or more, the interface between the aqueous phase and the methyl isobutyl ketone phase was not clear, although visually observable. Since it was necessary to collect the methyl isobutyl ketone phase such that the intermediate phase was not mixed therein, the amount of the carboxylic acid extract collected decreased compared to that of Example 2.

The results of Examples 1 and 2 as well as Comparative Examples 1 and 2 show that passing the carboxylic acid-containing fermentation broth through the nanofiltration membrane allows phase separation to occur clearly and quickly when performing extraction, and enables collection of a carboxylic acid extract phase-separated from the aqueous phase.

Example 3

A quantity of 1 L of the carboxylic acid-containing fermentation broth prepared in Reference Example 1 was passed through a microfiltration membrane (a porous membrane having a pore size of 0.01 μm or more and less than 1 μm, manufactured by Toray Industries, Inc.), and then concentrated sulfuric acid (manufactured by Sigma-Aldrich Co. LLC) was added thereto to adjust the pH to 4.0. Subsequently, the resultant was passed through an ultrafiltration membrane (molecular weight cutoff 10,000; manufactured by Toray Industries, Inc.). Thereafter, the nanofiltration membrane treatment and extraction were carried out in the same manner as in Example 1, to obtain a carboxylic acid extract (acetic acid extraction rate: 99%, succinic acid extraction rate: 90%). Formation of an intermediate phase containing solids between the aqueous phase and the ethyl acetate phase was not observed, in the above extraction, and the phase separation occurred extremely quickly within 10 seconds.

Comparative Example 3

The same procedure as in Example 3 was carried out, except that the nanofiltration membrane treatment was not performed, to obtain a carboxylic acid extract (acetic acid extraction rate: 90%, succinic acid extraction rate: 65%). In this extraction, an intermediate phase containing solids was formed between the aqueous phase and the ethyl acetate phase. Further, it took 10 minutes until a clear phase separation was observed.

The results of Example 3 and Comparative Example 3 show that the effect of the nanofiltration membrane is clearly observed, even when the pH of the carboxylic acid-containing fermentation broth is adjusted at a timing before passing the fermentation broth through the ultrafiltration membrane.

3-Hydroxyadipic acid-3,6-lactone and α-hydromuconic acid used in Reference Example 20 were produced by the methods described in the specification of WO 2016/068108.

Reference Example 20: Preparation of Various Carboxylic Acid-Containing Fermentation Broths Instead of adding acetic acid and succinic acid as in Reference Example 1, itaconic acid (manufactured by FUJIFILM Wako Pure Chemical Corporation), adipic acid (manufactured by FUJIFILM Wako Pure Chemical Corporation), 3-hydroxyadipic acid-3,6-lactone, α-hydromuconic acid, cis,cis-muconic acid (manufactured by Sigma-Aldrich Co. LLC.), 4-hydroxybenzoic acid (manufactured by FUJIFILM Wako Pure Chemical Corporation), or L-phenylalanine (manufactured by FUJIFILM Wako Pure Chemical Corporation) was added, to prepare each of the carboxylic acid-containing fermentation broths. The concentrations of itaconic acid, adipic acid, 3-hydroxyadipic acid-3,6-lactone and L-phenylalanine were each adjusted to 10 g/L. The concentrations of α-hydromuconic acid and cis,cis-muconic acid were each adjusted to 0.2 g/L. The concentration of 4-hydroxybenzoic acid was adjusted to 2 g/L.

Reference Examples 21 to 41

Each of the carboxylic acid-containing fermentation broths prepared in Reference Example 20 was passed through a microfiltration membrane (a porous membrane having a pore size of 0.01 μm or more and less than 1 μm, manufactured by Toray Industries, Inc.), and then passed through an ultrafiltration membrane (molecular weight cut-off: 10,000; manufactured by Toray Industries, Inc.). For each Reference Example, 1 L of the resulting carboxylic acid-containing fermentation broth was transferred to a raw water tank and passed once through the nanofiltration membrane under the nanofiltration membrane treatment conditions 1 described above. Each resulting carboxylic acid-containing filtrate lost its color, and was a clear aqueous solution. For each filtrate, the concentration of the carboxylic acid was analyzed by HPLC, and the permeability of the carboxylic acid was calculated by the following equation. The results of the permeability calculations are shown in Table 3.

Permeability (%)=(compound concentration in permeate)/(compound concentration in raw water)×100.

TABLE 3

Nanofiltration Membrane Permeation Tests of Various Carboxylic Acid-containing Fermentation broths

| | Carboxylic acid | pH | Filtration pressure (MPa) | Permeability (%) |
|---|---|---|---|---|
| Reference Example 21 | Itaconic acid | 4.0 | 0.5 | 55 |
| Reference Example 22 | Itaconic acid | 4.0 | 1.0 | 41 |
| Reference Example 23 | Itaconic acid | 4.0 | 1.5 | 36 |
| Reference Example 24 | Adipic acid | 4.0 | 0.5 | 61 |
| Reference Example 25 | Adipic acid | 4.0 | 1.0 | 50 |
| Reference Example 26 | Adipic acid | 4.0 | 1.5 | 45 |
| Reference Example 27 | 3-Hydroxyadipic acid-3,6-lactone | 4.0 | 0.5 | 89 |
| Reference Example 28 | 3-Hydroxyadipic acid-3,6-lactone | 4.0 | 1.0 | 76 |
| Reference Example 29 | 3-Hydroxyadipic acid-3,6-lactone | 4.0 | 1.3 | 71 |
| Reference Example 30 | α-Hydromuconic acid | 4.0 | 0.5 | 92 |
| Reference Example 31 | α-Hydromuconic acid | 4.0 | 1.0 | 86 |
| Reference Example 32 | α-Hydromuconic acid | 4.0 | 1.3 | 84 |
| Reference Example 33 | cis,cis-Muconic acid | 4.0 | 0.5 | 38 |
| Reference Example 34 | cis,cis-Muconic acid | 4.0 | 1.0 | 26 |
| Reference Example 35 | cis,cis-Muconic acid | 4.0 | 1.5 | 23 |
| Reference Example 36 | 4-Hydroxybenzoic acid | 4.0 | 0.5 | 70 |
| Reference Example 37 | 4-Hydroxybenzoic acid | 4.0 | 1.0 | 64 |
| Reference Example 38 | 4-Hydroxybenzoic acid | 4.0 | 1.5 | 62 |
| Reference Example 39 | L-phenylalanine | 4.0 | 0.5 | 21 |
| Reference Example 40 | L-phenylalanine | 4.0 | 1.0 | 9 |
| Reference Example 41 | L-phenylalanine | 4.0 | 1.5 | 6 |

Reference Examples 42 to 48

A quantity of 20 mL of each of the carboxylic acid-containing filtrates prepared in Reference Examples 22, 25, 28, 31, 34, 37 and 40 was transferred to a separatory funnel made of glass (capacity: 100 mL), and 20 mL of ethyl acetate (manufactured by FUJIFILM Wako Pure Chemical Corporation) was added thereto, followed by shaking 30 times. For each Reference Example, the concentration of the carboxylic acid in the aqueous phase was measured by HPLC, after shaking, and the extraction rate of the carboxylic acid was calculated by the following equation. The results are shown in Table 4.

Extraction rate (%)=(1−(concentration of compound to be extracted in raffinate)/(concentration of compound to be extracted before extraction))×100.

TABLE 4

Carboxylic Acid Extraction Tests from Carboxylic Acid-containing Filtrates

| | Carboxylic acid | pH | Extraction solvent | Extraction rate (%) |
|---|---|---|---|---|
| Reference Example 42 | Itaconic acid | 4.0 | Ethyl acetate | 14 |
| Reference Example 43 | Adipic acid | 4.0 | Ethyl acetate | 43 |
| Reference Example 44 | 3-Hydroxyadipic acid-3,6-lactone | 4.0 | Ethyl acetate | 64 |
| Reference Example 45 | α-Hydromuconic acid | 4.0 | Ethyl acetate | 87 |
| Reference Example 46 | cis,cis- Muconic acid | 4.0 | Ethyl acetate | 44 |
| Reference Example 47 | 4-Hydroxybenzoic acid | 4.0 | Ethyl acetate | 93 |
| Reference Example 48 | L-phenylalanine | 4.0 | Ethyl acetate | 76 |

Example 4

An experiment was carried out in the same manner as in Example 1, except that the itaconic acid-containing fermentation broth prepared in Reference Example 20 was used, to obtain an itaconic acid extract (extraction rate: 45%). Formation of an intermediate phase containing solids between the aqueous phase and the ethyl acetate phase was barely observed, in the above extraction, and the phase separation occurred extremely quickly within 10 seconds.

Example 5

An experiment was carried out in the same manner as in Example 1, except that the adipic acid-containing fermentation broth prepared in Reference Example 20 was used, to obtain an adipic acid extract (extraction rate: 90%). Formation of an intermediate phase containing solids between the aqueous phase and the ethyl acetate phase was barely observed, in the above extraction, and the phase separation occurred extremely quickly within 10 seconds.

Example 6

An experiment was carried out in the same manner as in Example 1, except that the 3-hydroxyadipic acid-3,6-lactone-containing fermentation broth prepared in Reference Example 20 was used, to obtain a 3-hydroxyadipic acid-3,6-lactone extract (extraction rate: 99%). Formation of an intermediate phase containing solids between the aqueous phase and the ethyl acetate phase was barely observed, in the above extraction, and the phase separation occurred extremely quickly within 10 seconds.

Example 7

An experiment was carried out in the same manner as in Example 1, except that the α-hydromuconic acid-containing fermentation broth prepared in Reference Example 20 was used, to obtain an α-hydromuconic acid extract (extraction rate: 99%). Formation of an intermediate phase containing solids between the aqueous phase and the ethyl acetate phase was barely observed, in the above extraction, and the phase separation occurred extremely quickly within 10 seconds.

Example 8

An experiment was carried out in the same manner as in Example 1, except that the cis,cis-muconic acid-containing fermentation broth prepared in Reference Example 20 was used, to obtain a cis,cis-muconic acid extract (extraction rate: 85%). Formation of an intermediate phase containing solids between the aqueous phase and the ethyl acetate phase was barely observed, in the above extraction, and the phase separation occurred extremely quickly within 10 seconds.

Example 9

An experiment was carried out in the same manner as in Example 1, except that the 4-hydroxybenzoic acid-containing fermentation broth prepared in Reference Example 20 was used, to obtain a 4-hydroxybenzoic acid extract (extraction rate: 99%). Formation of an intermediate phase containing solids between the aqueous phase and the ethyl acetate phase was barely observed, in the above extraction, and the phase separation occurred extremely quickly within 10 seconds.

Example 10

An experiment was carried out in the same manner as in Example 1, except that the L-phenylalanine-containing fermentation broth prepared in Reference Example 20 was used, to obtain an L-phenylalanine extract (extraction rate: 99%). Formation of an intermediate phase containing solids between the aqueous phase and the ethyl acetate phase was barely observed, in the above extraction, and the phase separation occurred extremely quickly within 10 seconds.

The results of Examples 1 to 10 show that our methods can be used in the recovery of various carboxylic acids.

The invention claimed is:

1. A method of producing a carboxylic acid, comprising:

(A') removing insoluble substances from a carboxylic acid-containing fermentation broth;

(A) filtering said insoluble substances-removed carboxylic acid-containing fermentation broth by passing said insoluble substances-removed carboxylic acid-containing fermentation broth through a nanofiltration membrane to obtain an aqueous carboxylic acid-containing filtrate that is free of organic solvent from a permeate side of said nanofiltration membrane and to accelerate phase separation between an aqueous phase and an organic phase in step (B); and (B) mixing said carboxylic acid-containing filtrate obtained in step (A) with an extraction solvent which undergoes the phase separation with said carboxylic acid-containing filtrate, and collecting a carboxylic acid extract phase-separated from the aqueous phase.

2. The method according to claim 1, wherein said carboxylic acid-containing fermentation broth and/or said carboxylic acid-containing filtrate is adjusted to a pH of 4.5 or less.

3. The method according to claim 1, wherein said step of removing the insoluble substances is a step of passing said carboxylic acid-containing fermentation broth through a microfiltration membrane.

4. The method according to claim 1, wherein said carboxylic acid to be produced is acetic acid, succinic acid, itaconic acid, adipic acid, 3-hydroxyadipic acid, 3-hydroxyadipic acid-3,6-lactone, α-hydromuconic acid, muconic acid, 4-hydroxybenzoic acid, phenylalanine, tyrosine, or histidine.

* * * * *